United States Patent
Funakura et al.

(10) Patent No.: US 11,952,497 B2
(45) Date of Patent: Apr. 9, 2024

(54) PHYCOCYANIN PIGMENT COMPOSITION

(71) Applicant: DIC Corporation, Tokyo (JP)

(72) Inventors: Seiji Funakura, Kamisu (JP); Takashi Shibano, Kamisu (JP); Hiroshi Sekikawa, Kamisu (JP)

(73) Assignee: DIC CORPORATION, Tokyo (JP)

( * ) Notice: Subject to any disclaimer, the term of this patent is extended or adjusted under 35 U.S.C. 154(b) by 53 days.

(21) Appl. No.: 17/912,183

(22) PCT Filed: Mar. 18, 2021

(86) PCT No.: PCT/JP2021/010972
§ 371 (c)(1),
(2) Date: Sep. 16, 2022

(87) PCT Pub. No.: WO2021/200182
PCT Pub. Date: Oct. 7, 2021

(65) Prior Publication Data
US 2023/0139450 A1    May 4, 2023

(30) Foreign Application Priority Data

Apr. 2, 2020    (JP) .................................. 2020-066714

(51) Int. Cl.
*C09B 61/00*    (2006.01)
*C09B 67/00*    (2006.01)

(52) U.S. Cl.
CPC ............ *C09B 61/00* (2013.01); *C09B 68/423* (2013.01)

(58) Field of Classification Search
CPC ..... C09B 61/00; C09B 68/423; C09B 67/006; C09B 67/0092; A61K 2800/612; A61K 8/0241; A61K 8/27; A61K 8/645; A61K 8/29; A61K 8/26; A61Q 1/02; C08K 9/04; C09D 11/322; C09D 7/41; C09D 7/62; C09D 11/037

USPC .......................................................... 8/637.1
See application file for complete search history.

(56) References Cited

FOREIGN PATENT DOCUMENTS

| FR | 2929957 A1 | * 10/2009 | ............ A61Q 19/00 |
|---|---|---|---|
| JP | 56-63911 A | 5/1981 | |
| JP | 57-117566 A | 7/1982 | |
| JP | 62-6691 A | 1/1987 | |
| JP | 1-123865 A | 5/1989 | |
| JP | 5-32909 A | 2/1993 | |
| JP | 11-299450 A | 11/1999 | |
| JP | 2001-323263 A | 11/2001 | |
| JP | 2006-230272 A | 9/2006 | |
| JP | 2016-89139 A | 5/2016 | |
| WO | WO 2014029352 A1 | * 2/2014 | ............... A61Q 5/10 |

OTHER PUBLICATIONS

International Search Report dated May 18, 2021, issued in counterpart International Application No. PCT/JP2021/010972 (3 pages).
Notice of Reasons for Refusal dated Jan. 25, 2022, issued in counterpart JP Patent Application No. 2021-568986, w/English translation (10 pages).

* cited by examiner

*Primary Examiner* — Eisa B Elhilo
(74) *Attorney, Agent, or Firm* — WHDA, LLP

(57) ABSTRACT

An object of the present invention is to provide a phycocyanin pigment composition insoluble in water and provide food, cosmetics, a coating material or a printing marker for pharmaceuticals or agricultural chemicals, a stationery product, a writing tool, a printing ink, an inkjet ink, a metal ink, a paint, a plastic coloring agent, a color toner, a fluorescent labeling agent, a fluorescent probe, or a chemical sensor, each containing the pigment composition. It was found that the phycocyanin pigment composition containing phycocyanin and a metal or a metal compound was insoluble in water, and thus the present invention was accomplished.

10 Claims, No Drawings

PHYCOCYANIN PIGMENT COMPOSITION

TECHNICAL FIELD

The present invention relates to a pigment composition.

BACKGROUND ART

As natural pigments, various types of red pigments, yellow pigments and blue pigments are present. In recent years, synthetic coloring agents have been regarded as problematic in terms of carcinogenicity or the like, and greater expectations have been placed on natural pigments, which are considered to have a higher level of safety. However, natural pigments have advantages and disadvantages in physical properties. Under the current circumstances, particularly, red and blue pigments assuming vivid color tones are less present.

As a natural pigment assuming a blue color, there is phycocyanin as an algal pigment. A phycocyanin pigment is a protein-binding pigment, and it is known that the phycocyanin pigment can be extracted from, for example, spirulina belonging to cyanobacteria. The phycocyanin pigment assumes a vivid blue color, and higher expectations of the market have been placed on the phycocyanin pigment as a sustainable pigment.

However, as described above, the phycocyanin pigment is a protein-binding pigment and hence water-soluble, and it has been clear that, when used in cosmetics or as a food pigment, the phycocyanin pigment is prone to dissolve in water and cause discoloring associated with the dissolution. Therefore, under the current circumstances, the phycocyanin pigment is used only in very limited applications.

The inventors investigated literatures describing solutions to the problems of the dissolution of the phycocyanin pigment in water and discoloring, that is, the way of improvement of water solubility, and found examples of adding tocopherol, ascorbic acid, or the like to natural pigments and examples of adding chlorogenic acids as a tannin component contained in coffee beans to natural pigments. (see PTLs 1, 2, and 3). However, according to any of the above-mentioned examples, the heat stability of natural pigment can be improved, but the water solubility thereof cannot be improved. There is no example in which the water solubility of the phycocyanin pigment can be improved, and such improvement has been desired.

CITATION LIST

Patent Literature

PTL 1: Japanese Unexamined Patent Application Publication No. S57-117566
PTL 2: Japanese Unexamined Patent Application Publication No. H05-32909
PTL 3: Japanese Unexamined Patent Application Publication No. 2001-323263

SUMMARY OF INVENTION

Technical Problem

An object of the present invention is to provide a pigment composition insoluble in water and provide food, cosmetics, a coating material or a printing marker for pharmaceuticals or agricultural chemicals, a stationery product, a writing tool, a printing ink, an inkjet ink, a metal ink, a paint, a plastic coloring agent, a color toner, a fluorescent labeling agent, a fluorescent probe, or a chemical sensor, each containing the pigment composition.

Solution to Problem

The inventors conducted extensive studies to solve the above-mentioned problem, and, as a result, found that a pigment composition containing phycocyanin and a metal or a metal compound was insoluble in water, and thus accomplished the present invention.

In other words, the present invention encompasses the following aspects.

[1] A water-insoluble pigment composition containing: phycocyanin, and a metal or a metal compound.

[2] The water-insoluble pigment composition according to [1], in which the metal or the metal compound is coated with the phycocyanin.

[3] The water-insoluble pigment composition according to [1] or [2], in which the composition mass ratio of the phycocyanin to the metal or the metal compound is the phycocyanin: the metal or the metal compound=0.1:99.9 to 90:10.

[4] The water-insoluble pigment composition according to any one of [1] to [3], in which the metal compound is a metal hydroxide or a metal oxide.

[5] The water-insoluble pigment composition according to any one of [1] to [4], in which a metal element constituting the metal or the metal compound is at least one metal element selected from aluminum, titanium, and zinc.

[6] Food, cosmetics, a coating material or a printing marker for pharmaceuticals or agricultural chemicals, a stationery product, a writing tool, a printing ink, an inkjet ink, a metal ink, a paint, a plastic coloring agent, a color toner, a fluorescent labeling agent, a fluorescent probe, or a chemical sensor, each containing the water-insoluble pigment composition according to any one of [1] to [5].

Advantageous Effects of Invention

According to the present invention, a pigment composition insoluble in water can be provided.

DESCRIPTION OF EMBODIMENTS

Hereinafter, a water-insoluble pigment composition according to the present invention will be described in detail, but the following descriptions about constituents are merely examples as embodiments of the present invention, and the present invention is not limited by the descriptions.

Phycocyanin

Phycocyanin used in the present invention is a protein-binding pigment and contains phycocyanobilin as a chromophore. Phycocyanin has a structure in which phycocyanobilin is bound to a protein.

Examples of the phycocyanin according to the present invention include algae phycocyanin, such as cyanobacteria phycocyanin, red algae phycocyanin, and cryptophyte phycocyanin. Among them, cyanobacteria phycocyanin is preferable because cyanobacteria phycocyanin can be collected in large amounts.

Examples of the cyanobacteria include cyanobacteria of the genus *Spirulina*, the genus *Arthrospira*, the genus

*Aphanizomenon*, the genus *Fisherella*, the genus *Anabaena*, the genus *Nostoc*, the genus *Synechocystis*, the genus *Synechococcus*, the genus *Tolypothrix*, the genus *Aphanothece*, the genus *Mastigoclaus*, and the genus *Pleurocapsa*. Among them, cyanobacteria of the genus *Spirulina* and the genus *Arthrospira*, which have been produced on an industrial scale and the safety of which has been confirmed, are preferable, and cyanobacteria of the genus *Spirulina* are more preferable.

As a raw material for preparing the phycocyanin, fresh cyanobacteria or dried cyanobacteria may be used. A dried cyanobacteria product may be obtained by drying fresh cyanobacteria according to the usual method, or a commercially available dried cyanobacteria product can be used.

The phycocyanin can be obtained, for example, by suspending cyanobacteria in water or a buffer solution such as a phosphate buffer solution or a citrate buffer solution, and extracting phycocyanin from the cyanobacteria.

A method for extracting the phycocyanin is not particularly limited, and a commonly known method can be used. Examples of a preferred embodiment of the extraction method include an extraction method described in Japanese Unexamined Patent Application Publication No. 2006-230272. Specific examples of the extraction method include an extraction method (i) described below. Using the extraction method (i), high-purity phycocyanin assuming a vivid color tone can be obtained.

<Extraction Method (i)>

The extraction method (i) includes:

a first step of obtaining a liquid extract in which phycocyanin in cyanobacteria is extracted into an aqueous suspension;

a second step of allowing a calcium salt to react with a phosphate in the liquid extract to produce calcium phosphate and causing the calcium phosphate to adsorb phycocyanin contaminants, thereby obtaining an adsorbate; and a third step of removing a cyanobacterial residue and the adsorbate from the liquid extract.

Furthermore, the above-described extraction method (i) is more preferably an extraction method (ii) described below.

<Extraction Method (ii)>

The extraction method (ii) includes:

a first step of obtaining a liquid extract in which phycocyanin in cyanobacteria is extracted into an aqueous suspension;

a second step of allowing a calcium salt to react with a phosphate in the liquid extract to produce calcium phosphate and causing the calcium phosphate to adsorb phycocyanin contaminants, thereby obtaining an adsorbate;

a third step of removing a cyanobacterial residue and the adsorbate from the liquid extract; and a step of, prior to the third step, adding a chelating agent to the liquid extract.

The phycocyanin used in the present invention was obtained from a commercial product, LINABLUE G1 (manufactured by DIC LIFETEC Co., Ltd., trehalose: 55%, phycocyanin pigment: 40%, trisodium citrate: 5%), in which phycocyanin was mixed with a stabilizing agent. As described in Japanese Unexamined Patent Application Publication No. H11-299450, trehalose is used to increase thermal stability and citric acid is used as a pH adjuster.

Metal and Metal Compound

Examples of a metal element in the metal or the metal compound used in the present invention include metal elements of Group 1 to Group 15 in the periodic table of elements, excluding metal elements of Period I and Period II. Among them, metal elements, such as iron, cobalt, nickel, zinc, aluminum, and titanium, can be used, and at least one metal elements selected from the above-mentioned metal elements can be used. A metal or a metal compound having no effect on the human body particularly in food and cosmetic applications is preferably used. In the present embodiment, aluminum, titanium, and zinc are particularly preferably used.

In the present embodiment, to achieve stronger physical adsorption of phycocyanin onto a metal or a metal compound, a metal hydroxide and a metal oxide are preferably used as the metal or the metal compound, and aluminum hydroxide, titanium dioxide, and zinc oxide are particularly preferably used. A slurry of aluminum hydroxide, titanium dioxide, zinc hydroxide, or the like obtained by adding alkali to a chloride, such as aluminum chloride, titanium tetrachloride, or zinc chloride, is preferably used because such slurry has stronger physical adsorption onto phycocyanin. Furthermore, to achieve further stronger physical adsorption, a metal or a metal compound having a surface coated with phycocyanin is more preferable. Coating is defined as a state in which phycocyanin is partially or uniformly present on the metal surface and covers the metal surface.

A preferable particle size of particles of the metal or the metal compound depends on applications, and also a hue depends on the particle size of the metal or the metal compound. For example, the particle size is preferably 50 nm to 20 μm in applications in food and cosmetics, while the particle size is preferably 50 to 500 nm in applications in others.

Water Insoluble Pigment Composition

Phycocyanin as a simple substance is originally in the form of a dye and hence water-soluble. In contrast, in the present invention, it was found that, when phycocyanin strongly adsorbed onto the surfaces of particles of a metal or a metal compound, a pigment composition containing the phycocyanin and the particles of the metal or the metal compound was formed, so that the pigment composition was water-insoluble. With the insolubility achieved according to the present invention, phycocyanin, which has been limited to be used as a blue pigment in food and cosmetic applications, has a tolerance enough to be used, as a coloring material equivalent to a common pigment, for applications to food, cosmetics, a coating material or a printing marker for pharmaceuticals or agricultural chemicals, a stationery product, a writing tool, a printing ink, an inkjet ink, a metal ink, a paint, a plastic coloring agent, a color toner, a fluorescent labeling agent, a fluorescent probe, a chemical sensor, or the like. Furthermore, with the insolubility, improvement of properties such as heat resistance and light resistance can be expected. Note that the applications of the water-insoluble pigment composition according to the present invention are not limited to the above-mentioned applications.

In the water-insoluble pigment composition according to the present invention, the composition mass ratio of the phycocyanin to the metal or the metal compound can be designed arbitrarily, and the water-insoluble pigment composition can be used by setting a ratio of the phycocyanin:the metal or the metal compound=0.1:99.9 to 10:90. The mass ratio is preferably the phycocyanin:the metal or the metal compound=1:99 to 70:30.

Method for Producing Water-Insoluble Pigment Composition

As a method for producing the water-insoluble pigment composition according to the present invention, a method of mixing phycocyanin with particles of the metal or the metal compound in a solvent is preferable because this method makes it possible to produce the most uniform water-insoluble pigment composition.

Examples of the method for producing the water-insoluble pigment composition by which substances are mixed in a solvent include a method in which 1) a dispersion of the metal or the metal compound is produced first, (2) meanwhile, phycocyanin or a preparation containing phycocyanin is dissolved in water to produce an aqueous solution, (3) next, the above-mentioned two liquids are mixed to prepare a water-insoluble pigment composition, and (4) the obtained mixed solution containing the water-insoluble pigment composition is filtered and dried. The mixing may be performed at a room temperature or may be performed with heating. From the viewpoint of the decomposition temperature of the phycocyanin as a single substance, the mixing is performed preferably at 10° C. to 60° C., and more preferably at 20° C. to 50° C.

As a method for mixing the metal or the metal compound and phycocyanin, a phycocyanin-containing solution may be mixed with a water dispersion of the metal or the metal compound, or, on the contrary, a water dispersion of the metal or the metal compound may be mixed with a phycocyanin-containing solution, or alternatively, these two solutions may be mixed little by little for preparation. The metal or the metal compound in powder or phycocyanin in powder may be added to a liquid containing the metal, the metal compound, or phycocyanin, or alternatively the metal powder or the metal compound powder may be mixed with the phycocyanin powder, and water may be added to the resulting mixture. The mixing may be performed at a room temperature or may be performed with heating. From the viewpoint of the decomposition temperature of the phycocyanin as a single substance, the mixing is performed preferably at 10° C. to 60° C., and more preferably at 20° C. to 50° C. The range of pH for mixing the metal or the metal compound with the phycocyanin-containing solution is adjusted to preferably 3.0 to 8.0, and more preferably 4.0 to 7.5.

Examples of a pH adjustor for adjusting the pH include hydrochloric acid, citric acid, acetic acid, and lactic acid. The range of pH of at mixed solution in the case of adding a pH adjuster thereto is adjusted to preferably 3.0 to 5.0 and more preferably 3.5 to 5.0 from the viewpoint of efficient adsorption of phycocyanin onto the metal or the metal compound in the mixed solution and insolubilization of phycocyanin.

By filtering and drying the obtained mixed solution, the water-insoluble pigment composition can be obtained. When the mixed solution is filtered through a filter such as Nutsche, it can be confirmed whether there is no coloration in a filtrate and that phycocyanin as a pigment adsorbs onto the metal or the metal compound. Furthermore, a wet cake of the water-insoluble pigment composition repeatedly washed with water, and similarly, it can be confirmed whether the filtrate is clear and colorless and that the pigment component has not leaked out. The obtained water-containing wet cake of the water-insoluble pigment composition is dried at a room temperature, by heating, by vacuum, or by vacuum-drying, whereby a water-insoluble pigment composition cart be obtained. Any drying method and any dryer can be used for the drying as long as the method and the dryer are usual ones, and the method and the dryer are not limited to particular ones.

The water-insoluble pigment compositions according to the present invention may be a water-insoluble pigment composition in the form of the above-mentioned water-containing wet cake or may be a dried water-insoluble pigment composition, and thus can be used properly, depending on the applications. When used in a water dispersion or ink, the wet cake can be used as it is, meanwhile, when the wet cake of the water-insoluble pigment composition is used in a solvent dispersion system, the wet cake can be used after changed from a water base to a solvent base. The dry water-insoluble pigment composition can be used as it is, or of course can be redispersed in water, an organic solvent, a resin solution, or the like.

Stabilizers, Additives

Of course other organic and inorganic pigments, dyes, and pigments can be mixed with the water-insoluble pigment composition according to the present invention at any ratio, and a desired and required hue can be achieved. A stabilizer and an additive can be added to the water-insoluble pigment composition according to the present invention for the purpose of giving higher light-resistance and higher heat-resistance.

A stabilizer or an additive can be added to either or both of an aqueous solution of the metal or the metal compound and a phycocyanin-containing solution or may be added to the produced water-insoluble pigment composition.

The water-insoluble pigment composition according to the present invention is mixed with other resins, a rubber, an additive, a pigment, a dye, or the like, as needed, so that the resulting mixture is adjusted to be a final product, such as food, cosmetics, a coating material or a printing marker for pharmaceutical or agricultural chemicals, a stationery product, a writing tool, a printing ink, an inkjet ink, a metal ink, a paint, a plastic coloring agent, a color toner, a fluorescent labeling agent, a fluorescent probe, or a chemical sensor. Examples of the above-mentioned applications will be described below.

Cosmetics Applications

The water-insoluble pigment composition according to the present invention can be used in cosmetics. The water-insoluble pigment composition is not limited to be used in particular cosmetics, but can be used in various types of cosmetics.

The cosmetics may be any type of cosmetics as long as the cosmetics can effectively perform functions. The cosmetics may be in the form of a lotion, a cream gel, a spray, or the like. Examples of the cosmetics include: skin care cosmetics, such as facial cleanser, a make-up remover, a lotion, an essence, a pack, a protective emulsion, a protective cream, whitening cosmetics, and UV-protective cosmetics; make-up cosmetics, such as a foundation, white powder, a makeup base, a lipstick, eye makeup, a cheek rouge, and a nail enamel; hair care cosmetics, such as a shampoo, a hair rinse, a hair treatment, a hairdressing, a permanent wave agent, a hair dye, and a hair growth tonic; and body care cosmetics, such as body wash cosmetics, deodorant cosmetics, and a bath agent.

The amount of the water-insoluble pigment composition accord to the present invention to be used in the cosmetics can be suitably set in accordance with the type of the cosmetics. The amount of the water-insoluble pigment composition contained in the cosmetics usually in a range of 0.1% to 99% by mass, and is generally preferably in a range of 0.1% to 10% by mass. In contrast, in the make-up cosmetics with the objective of coloring, the amount of the water-insoluble pigment composition is preferably in a range of 5% to 80% by mass, more preferably in a range of 10% to 70% by mass, and most referably a range of 20% to 60% by mass. When the amount of the water-insoluble pigment composition according to the present invention contained in the cosmetics is within the above-mentioned range, a function such as coloring performance can be effectively performed and also a function required for the cosmetics can be retained.

Besides the water-insoluble pigment composition according to the present invention, the cosmetics may contain, depending on the type of the cosmetics, other acceptable cosmetic ingredients, such as a carrier, a pigment, oil, sterol, amino acid, a moisturizer, powder, a coloring agent, a pH adjuster, a fragrance, essential oil, a cosmetic active ingredient, a vitamin, an essential fatty acid, sphingolipid, a self-tanning agent, an excipient, a filler, an emulsifier, an antioxidant, a surfactant, a chelating agent, a gelling agent, a thickening agent, an emollient, a humectant, a moisturizer, a mineral, a viscosity modifying agent, a flow control agent, a keratolytic agent, retinoid, a hormonal compound, an alpha-hydroxy acid, an alpha-keto acid, an antimycobacterial agent, an antifungal agent, an antibacterial agent, an antiviral agent, a painkiller, an antiallergic agent, an antihistamine, an anti-inflammatory agent, an anti-irritant, an anti-tumor drug, an immune system boosting agent, an immune system inhibiting agent, an anti-acne agent, an anesthetic, a disinfectant, an insect repellent, a skin cooling compound, a skin barrier, a skin penetration enhancer, an exfoliant, a lubricant, an aromatic, a dye, a decoloring agent, a hypopigmenting agent, a preservative, a stabilizer, pharmaceuticals, a light stabilizer, and spherical powder.

The above-mentioned cosmetics can be produced by mixing the water-insoluble pigment composition according to the present invention with other cosmetic ingredients. Cosmetics containing the water-insoluble pigment composition according to the present invention can be used in the same way as for common cosmetics, for example, depending on the type of the cosmetics.

Ink and Paint Applications

The water-insoluble pigment composition according to the present invention can be used as an ink or a paint. Note that applications and compositions of the ink and the paint will be described, but are not limiting. The water-insoluble pigment composition according to the present invention may be dispersed only in a thermoplastic resin, but can be dispersed in a printing ink vehicle or a paint vehicle that contains a thermoplastic resin as an essential ingredient.

As for the thermoplastic resin, for example, a polyester resin, a polyamide resin, a styrene resin, an acrylic resin, polyolefins, polyalkylene terephthalates, or a polyvinyl chloride resin can be used as a resin for dispersion.

For example, a planographic ink vehicle is produced from 20% to 50% (by mass) of a resin, such as a rosin-modified phenolic resin, a petroleum resin, or an alkyd resin; 0% to 30% (by mass) of animal fat or vegetable oil, such as linseed oil, tung oil, or soybean oil; 10% to 60% (by mass) of a solvent, such as n-paraffin, iso-paraffin, naphthene, or α-olefin, an aromatic; and a few percent (by mass) of an additive, such as a solubilizer or a gelling agent.

A gravure printing ink vehicle or a flexographic printing ink vehicle is produced, for example, from 10% to 50% (by mass) of at least one resin selected from rosins, a maleic acid resin, a polyamide resin, a vinyl resin, a cyclized rubber, a chlorinated rubber, an ethylene-vinyl acetate copolymer resin, a urethane resin, a polyester resin, an alkyd resin, nitrocellulose, cellulose acetate, and the like; and 30% to 80% (by mass) of a solvent, such as alcohols, toluene, n-hexane, ethyl acetate, cellosolve, or butyl cellosolve acetate.

A paint vehicle is produced from 20% to 80% (by mass) of a resin, such as an alkyd resin, an epoxy resin, an acrylic resin, a polyurethane resin, a polyester resin, a melamine resin, a urea resin, or a water-soluble resin; and 10% to 50% (by mass) of a solvent, such as hydrocarbons, alcohols, ketones, or water.

Plastic Applications

The water-insoluble pigment composition according to the present invention can be used for plastic coloring applications. To obtain a colored plastic molded product, a thermoplastic resin (plastic) for themoforming such as injection molding or press molding, for example, polyolefins or a polyvinyl chloride resin such as polyethylene or polypropylene is used. The water-insoluble pigment composition according to the present invention can be kneaded into the above-mentioned resin in a conventionally known manner.

Toner Applications

The water-insoluble pigment composition according to the present invention can also be used for toner coloring applications. To obtain an electrostatic image development toner, a thermoplastic resin being solid at a room temperature and having film forming properties, such as a polyester resin, a polyamide resin, a styrene resin, or an acrylic resin, is used as a dispersion resin.

The electrostatic image development toner produced using the water-insoluble pigment composition according to the present invention as a component can be used as a one-component color magnetic toner containing a magnetic substance in the toner (a color toner for magnetic one-component development), a non-magnetic one-component color toner containing no magnetic substance (a color toner for non-magnetic one-component development), or a color toner for a two-component color developer mixed with a carrier (a color toner for two-component development).

The one-component color magnetic toner can be formed from other additives, for example, a coloring agent, a binding resin, magnetic powder, a charge control agent (CCA), and a mold release agent, as is the case with a commonly used one-component color magnetic toner.

The amount of the water-insoluble pigment composition contained in the electrostatic charge image development toner is not particularly limited, but is preferably 0.5 to 25 parts by mass with respect to 100 parts by mass of the binding resin, and more preferably 4 to 10 parts by mass with respect to 100 parts by mass of the binding resin from the viewpoint of further enhancing the electrostatic properties of the coloring agent.

As the binding resin to be used for the electrostatic image development toner, any of the known and commonly used ones exemplified as the thermoplastic resin can be used, and any of synthetic resins, natural resins, natural rubbers, synthetic rubbers, synthetic waxes, and the like that exhibit adhesive properties under the application of heat or pressure can be used.

EXAMPLES

Hereinafter, the present invention will be described in more detail below with examples, but the scope of the present invention is not limited by these examples.

Example 1

In a 5-L glass beaker, 46.3 g of aluminum (III) chloride hexahydrate (manufactured by KANTO CHEMICAL CO., INC.) was dissolved in 1,200 mL of ion-exchanged water at a room temperature (20° C.), and 47.4 g of a 48% sodium hydroxide solution (manufactured by KANTO CHEMICAL CO., INC.) was added to achieve a pH of 6.0, whereby an aluminum hydroxide slurry was obtained. In 600 mL of ion-exchanged water, 37.5 g of LINABLUE G1 (manufactured by DIC LIFETEC Co., Ltd., trehalose: 55%, phycocyanin pigment: 40%, trisodium citrate: 5%) was dissolved with stirring, and the resulting LINABLUE G1 solution was added to the aluminum hydroxide slurry little by little at a room temperature (20° C.). When one drop of the resulting blue slurry was dropped onto a filter paper after stirring for 1 hour, it was observed that a portion in which the blue slurry was dropped colored circularly in blue, and then a colorless, transparent liquid spread concentrically, hence it was confirmed that the phycocyanin became insoluble. The blue slurry was filtered through a filter paper by using Nutsche, and washed with 2 L of ion-exchanged water. The rinse water was colorless. The resulting wet cake had a clear blue color. The wet cake was dried a vacuum dryer (740 mmHg) at a room temperature (20° C.) or 12 hours and then dried by a dryer at 50° C. for 5 hours to obtain 27.0 g of powder (1) in which aluminum hydroxide was coated with phycocyanin. The composition mass ratio of the phycocyanin pigment to the aluminum hydroxide in the powder (1), the composition mass ratio being determined by subtracting an amount of the aluminum hydroxide calculated based on a feeding amount from the yield of the powder (1), was the phycocyanin: the aluminum hydroxide=50:50. The obtained powder (1) had a blue color similar to the color of phycocyanin.

Example 2

In a 2-L glass beaker, 25.5 g of aluminum (III) chloride hexahydrate (manufactured by KANTO CHEMICAL CO., INC.) was dissolved in 858 mL of ion-exchanged water at a room temperature (20° C.), and a 5% sodium hydroxide solution prepared from a 48% sodium hydroxide solution (manufactured by KANTO CHEMICAL CO., INC.) was added to achieve a pH of 4.0, whereby an aluminum hydroxide slurry was obtained. To the slurry, 49.7 g of powder of LINABLUE G1 (manufactured by DIC LIFETEC. Co., Ltd., trehalose: 55%, phycocyanin pigment: 40%, trisodium citrate: 5%) was added, and stirred at a room temperature (20° C.) for 30 minutes. Subsequently, when a 5% sodium hydroxide solution was added to adjust the pH from 4.0 to 7.0, aluminum hydroxide was precipitated, whereby a blue slurry was obtained. When one drop of the resulting blue slurry was dropped onto a filter paper after stirring for 1 hour, it was observed that a portion in which the blue slurry was dropped colored circularly in blue, and then a colorless, transparent liquid spread concentrically, hence it was confirmed that the phycocyanin became insoluble. The blue slurry was filtered through a filter paper by using Nutsche, and washed with 2 L of ion-exchanged water to obtain a blue wet cake. The wet cake was dried by a vacuum dryer (740 mmHg) at a room temperature (20° C.) for 12 hours and then dried by a dyer at 50° C. for 5 hours to obtain 28.1 g of powder (2) in which aluminum hydroxide was coated with phycocyanin. The composition mass ratio of the phycocyanin pigment to the aluminum hydroxide in the powder (2), the composition mass ratio being determined by subtracting an amount of the aluminum hydroxide calculated based on a feeding amount from the yield of the powder (2), was the phycocyanin: the aluminum hydroxide=70:30. The obtained powder (2) had a blue color similar to the color of the phycocyanin.

Example 3

In a 500-mL glass beaker, 1.0 g of LINABLUE G1 (manufactured by DIC LIFETEC Co., Ltd., trehalose: 55%, phycocyanin pigment: 40%, trisodium citrate: 5%) was dissolved in 100 mL of ion-exchanged water at a room temperature (20° C.), and 3.8% hydrochloric acid prepared from hydrochloric acid (manufactured by KANTO CHEMICAL CO., INC.) was added to achieve a pH of 4.0. To the resulting solution, 1.6 g of titanium dioxide ultrafine particles (hydrophilic) (manufactured by Orangeflower Co., Ltd) was added, and stirred at a room temperature (20° C.) for 30 minutes. When one drop of the resulting blue slurry was dropped onto a filter paper, it was observed that a portion in which the blue slurry was dropped colored circularly in blue, and then a colorless, transparent liquid spread concentrically, hence it was confirmed that the phycocyanin became insoluble. The blue slurry was then filtered using Nutsche. and washed with ion-exchanged water until the pH of the rinse water became neutral, whereby a blue wet cake was obtained. The wet cake was dried by a vacuum dryer (740 mmHg) at a room temperature (20° C.) for 12 hours, and then dried by a dryer at 50° C. for 5 hours to obtain 1.6 g of powder (3) in which titanium dioxide was coated with phycocyanin. The composition mass ratio of the phycocyanin pigment and titanium oxide in the powder (3), the composition mass ratio being calculated from the feeding amounts of LINABLUE G1 and titanium oxide, was the phycocyanin: the titanium oxide=20:80. The obtained powder (3) had a blue color similar to the color of the phycocyanin.

Example 4

In a 1-L glass beaker, at a room temperature (20° C.), 1.0 g of zinc oxide (manufactured by Orangeflower Co., Ltd.) was added and dispersed in 300 mL of ion-exchanged water, and 3.8% hydrochloric acid prepared from hydrochloric acid (KANTO CHEMICAL CO., INC.) was added to achieve a pH of 4.0. At this moment, zinc oxide changed into zinc chloride and was dissolved in water. Subsequently, to the resulting solution, 250 mg of LINABLUE G1 (manufactured by DIC LIFETEC Co., Ltd., trehalose: 55%, phycocyanin pigment: 40%, trisodium citrate: 5%) was added, and stirred at a room temperature (20° C.) for 30 minutes. Next, a 5% sodium hydroxide solution was added to the solution to adjust the pH of the solution to 7.0. At this moment, zinc chloride changed into zinc hydroxide and precipitated and dyed with phycocyanin to obtain a blue slurry. When one drop of the resulting blue slurry was dropped onto a filter paper, it was observed that a portion in which the blue slurry was dropped colored circularly in blue, and then a colorless, transparent liquid spread concentrically, hence it was confirmed that the phycocyanin became insoluble. The blue slurry was then filtered using Nutsche, and washed with ion-exchanged water until the pH of the rinse water became neutral, whereby a blue wet cake was obtained. The wet cake was dried by a vacuum dryer (740 mmHg) at a room temperature (20° C.) for 12 hours, and then dried by a dryer at 140° C. for 5 hours to change the zinc hydroxide into zinc oxide, whereby 1.0 g of powder (4) in which the zinc oxide was coated with the phycocyanin. The composition mass ratio of the phycocyanin pigment and the zinc oxide in the powder (4), the composition mass ratio being calculated from feeding amounts of LINABLUE G1 and zinc oxide, was the phycocyanin: the zinc oxide=9:91. The obtained powder (4) had a blue color similar to the color of the phycocyanin.

Comparison Example 1

LINABLUE G1 prepared by a manufacturing method described in Japanese Unexamined Patent Application Publication No. H11-299450 was used. To 1.00 g of water, 10 mg of LINABLUE G1 was added and stirred for 5 minutes to prepare a dispersion (1). When one drop of the dispersion (1) was dropped onto a filter paper, it was conserved that a blue liquid uniformly concentrically spread around a portion in which the dispersion (1) was dropped. This indicates that, in the dispersion (1), LINABLUE G1 was dissolved in water, hence, LINABLUE G1 was soluble in water.

As is clear from Examples 1 to 4 and Comparative Example 1, phycocyanin is water-soluble, meanwhile the pigment composition containing phycocyanin and aluminum hydroxide, titanium oxide, or zinc oxide was water-insoluble.

The invention claimed is:
1. A water-insoluble pigment composition comprising:
phycocyanin; and
a metal or a metal compound,
wherein a composition mass ratio of the phycocyanin to the metal or the metal compound is the phycocyanin: the metal or the metal compound=0.1:99.9 to 90:10.

2. The water-insoluble pigment composition according to claim 1, wherein the metal or the metal compound is coated with the phycocyanin.
3. The water-insoluble pigment composition according to claim 1, wherein the metal compound is a metal hydroxide or a metal oxide.
4. The water-insoluble pigment composition according to claim 1, wherein a metal element constituting the metal or the metal compound is at least one metal element selected from aluminum, titanium, and zinc.
5. Food, cosmetics, a coating material or a printing marker for pharmaceuticals or agricultural chemicals, a stationery product, a writing tool, a printing ink, an inkjet ink, a metal ink, a paint, a plastic coloring agent, a color toner, a fluorescent labeling agent, a fluorescent probe, or a chemical sensor, each containing the water-insoluble pigment composition according to claim 1.
6. A water-insoluble pigment composition comprising:
phycocyanin; and
a metal or a metal compound,
wherein the metal compound is a metal hydroxide or a metal oxide.
7. The water-insoluble pigment composition according to claim 6, wherein the metal or the metal compound is coated with the phycocyanin.
8. The water-insoluble pigment composition according to claim 6, wherein
a composition mass ratio of the phycocyanin to the metal or the metal compound is the phycocyanin: the metal or the metal compound=0.1:99.9 to 90:10.
9. The water-insoluble pigment composition according to claim 6, wherein a metal element constituting the metal or the metal compound is at least one metal element selected from aluminum, titanium, and zinc.
10. Food, cosmetics, a coating material or a printing marker for pharmaceuticals or agricultural chemicals, a stationery product, a writing tool, a printing ink, an inkjet ink, a metal ink, a paint, a plastic coloring agent, a color toner, a fluorescent labeling agent, a fluorescent probe, or a chemical sensor, each containing the water-insoluble pigment composition according to claim 6.

* * * * *